US00PP25829P3

(12) United States Plant Patent
Bradford et al.

(10) Patent No.: US PP25,829 P3
(45) Date of Patent: Aug. 25, 2015

(54) NECTARINE TREE NAMED 'AUTUMN PEARL'

(50) Latin Name: *Prunus persica*
Varietal Denomination: Autumn Pearl

(71) Applicants: Lowell Glen Bradford, Le Grand, CA (US); Jon Michael Quisenberry, Merced, CA (US)

(72) Inventors: Lowell Glen Bradford, Le Grand, CA (US); Jon Michael Quisenberry, Merced, CA (US)

( * ) Notice: Subject to any disclaimer, the term of this patent is extended or adjusted under 35 U.S.C. 154(b) by 107 days.

(21) Appl. No.: 13/998,860

(22) Filed: Dec. 16, 2013

(65) Prior Publication Data

US 2015/0173275 P1 Jun. 18, 2015

(51) Int. Cl.
*A01H 5/08* (2006.01)

(52) U.S. Cl.
USPC ..... Plt./188

(58) Field of Classification Search
USPC ..... Plt./187, 188
See application file for complete search history.

(56) References Cited

U.S. PATENT DOCUMENTS

| | | | |
|---|---|---|---|
| PP13,475 | P2 | 1/2003 | Bradford |
| PP14,240 | P2 | 10/2003 | Bradford |
| PP24,835 | P3 | 9/2014 | Glen |

*Primary Examiner* — Susan McCormick Ewoldt

(57) ABSTRACT

The present invention relates to a new and distinct variety of nectarine tree, *Prunus persica,* broadly characterized by a medium size, moderately vigorous, hardy, self-fertile, productive and regular bearing tree. The variety blooms during the mid to late season and requires about 600 chilling hours. The tree produces a small blossom and reniform leaf glands. The fruit matures under the ecological conditions described in early September, with first picking on Sep. 1, 2013. The fruit has a bitter kernel and is medium in size, globose in shape, clingstone in type, firm in texture, white in flesh color, mostly red in skin color, and a very good tasting balance of low acid and sugar.

1 Drawing Sheet

Botanical classification: *Prunus persica.*
Variety denomination: 'Autumn Pearl'.

BACKGROUND OF THE VARIETY

In a continuing effort to improve the quality of shipping fruits, we, the inventors, typically hybridize a large number of peach, nectarine, plum, apricot, and cherry seedlings each year. We also grow a smaller number of open pollinated seeds of each of these fruits, usually to capture recessive traits. The present invention relates to a new and distinct variety of nectarine tree, which has been denominated varietally as 'Autumn Pearl'.

The present variety was hybridized by us in 2005 as a first generation cross using 'Giant Pearl' (U.S. Plant Pat. No. 14,240) nectarine as the selected seed parent and 'September Bright' (U.S. Plant Pat. No. 13,475) nectarine as the selected pollen parent. The fruit of this cross was gathered that summer, and the seeds were removed, cracked, stratified, germinated, and grown as seedlings on their own root in my greenhouse. Upon reaching dormancy the seedlings were transplanted as a group to a cultivated area of our experimental orchard located near Le Grand, Calif., in Merced County (San Joaquin Valley). During the fruit evaluation season of 2008 we selected the present variety as a single tree from the group of seedlings described above. Subsequent to origination of the present variety of nectarine tree, we asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was compatible and true to type.

The present variety is similar to its seed parent, 'Giant Pearl' (U.S. Plant Pat. No. 14,240) nectarine by being a medium size tree, by being self-fruitful, by having reniform leaf glands, and by producing nectarines that are firm, mostly red in skin color, white in flesh color, globose in shape, and clingstone in type, but is distinguished therefrom by producing fruit that matures about three weeks later, that is somewhat smaller in size, and that has a blend of acid and sugar rather than subacidic in taste.

The present variety is similar to its pollen parent, 'September Bright' (U.S. Plant Pat. No. 13,475) nectarine by being self-fruitful, by having reniform leaf glands, by having a small blossom, by having reniform leaf glands, and by producing nectarines that are firm, that are mostly red in skin color, that are globose in shape, that are clingstone in type, and that mature in early September, but is distinguished therefrom by producing fruit that is somewhat larger in size, and that has a blend of acid and sugar rather than acidic in flavor, that is much sweeter, and that is white instead of yellow in flesh color.

The present variety is most similar to 'Pearlicious XVII' (U.S. Plant Pat. No. 24,835) nectarine by being a medium size tree, by being self-fruitful, and by producing nectarines that are firm, mostly red in skin color, white in flesh color, sweet in flavor, globose in shape, and clingstone in type, but is distinguished therefrom by having a small blossom instead of large and by producing fruit that has a bitter instead of sweet kernel and that matures about one week later when compared side by side during the same year.

SUMMARY OF VARIETY

In summary, the present nectarine variety is characterized by a medium size, moderately vigorous, hardy, self-fertile, productive and regular bearing tree. The variety blooms during the mid to late season and requires about 600 chilling hours. The tree produces a small blossom and reniform leaf glands. The fruit matures under the ecological conditions described in early September, with first picking on Sep. 1, 2013. The fruit has a bitter kernel and is medium in size, globose in shape, clingstone in type, firm in texture, white in flesh color, mostly red in skin color, and a very good tasting balance of low acid and sugar.

DRAWING

The accompanying photograph consists of four whole fruits positioned to display the characteristics of the skin color and form, one sliced fruit to reveal the flesh and stone, two insets to reveal buds and blossoms, and characteristic leaves.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin Valley), Calif., and was developed at the state of firm ripe on Sep. 6, 2013, on the original tree during its eighth growing season. The blossom and flower descriptions were made the previous blooming season. All major color code designations are by reference to the Inter-Society Color Council, National Bureau of Standards. Common color names are also used occasionally.

It is to be noted that the 2013 fruit season in California was very warm during the spring and the ripening times of almost all varieties were about ten days earlier than other years.

PARENTAGE

Seed parent: 'Giant Pearl' (U.S. Plant Pat. No. 14,240) nectarine.

Pollen parent: 'September Bright' (U.S. Plant Pat. No. 13,475) nectarine.

TREE

Size: Medium, reaching and maintaining a height of 9' [2.74 m.] and a spread of 7' [2.13 m.] after eight growing seasons utilizing typical dormant pruning.

Vigor: Moderately vigorous, responding typically to irrigation and fertilization. The variety grows about 3' [0.91 m.] of surplus top-growth during the spring and summer. The plant should be grown on a standard commercial rootstock for production purposes.

Growth: Spreading and dense.

Form: Vase type.

Hardiness: Hardy with respect to central California winters.

Approximate chilling requirement: 600 hours.

Heat tolerance: Observed to perform adequately in typical central California climatic conditions, which typically include extended periods of heat.

Drought tolerance: Variety is developed for commercial orchards and requires regular irrigation.

Production: Productive, thinning necessary.

Fertility: Self-fertile.

Bearing: Regular bearer with no alternate bearing yet observed.

Trunk:

*Size.*—Medium, reaching a maximum diameter of 5" [127 mm.] after the eighth growing season.

*Texture.*—Medium shaggy.

*Bark color.*—A Grayish brown [61. gy.Br] and Dark grayish brown [62. d.gy.Br] variegation with Strong Brown [55. s.Br] crevices present.

*Lenticels.*—Approximate Number Per Square Inch: 10. Color: Strong yellowish brown [74. s.yBr]. Average Size: ⅛" [3.2 mm.]. Shape: Eye-shaped, elongated.

Branches:

*Size.*—Diameter of main scaffold is 2¾" [69.9 mm.] measured 12" above the crotch, Diameter of limb is 1½" [38.1 mm.] measured 12" above the first fork.

*Texture.*—Smooth on first year wood, increasing roughness with age.

*Color.*—Second Year Wood: Moderate yellowish brown [77. m.yBr] with Strong yellowish brown [74. s.yBr] crevices present.

*Lenticels.*—Number Per Square Inch: About 30 on second year wood. Color: Light yellowish brown [76. l.yBr]. Average size: 1/64" [0.4 mm.] on second year wood. Shape: Eye-shaped, elongated.

Leaves:

*Size.*—Medium. Average Length: 5¾" [146.1 mm.]. Average Width: 1⅜" [34.9 mm.].

*Arrangement.*—Alternate.

*Thickness.*—Medium.

*Form.*—Elliptical.

*Apex.*—Acuminate.

*Base.*—Rounded to obtuse.

*Surface.*—Smooth.

*Color.*—Dorsal Surface: Moderate olive green [125. m.OlG]. Ventral Surface: Moderate yellow green [120. m.YG].

*Margin.*—Finely serrate.

*Venation.*—Pinnately net veined.

*Vein color.*—Light yellow green [119. l.YG].

*Petiole.*—Average Length: 7/16" [11.1 mm.]. Average Thickness: 1/16" [1.6 mm.]. Color: Brilliant yellow green [116. brill.YG].

*Stipules.*—Number: Usually 2 per leaf, up to 6 per growing tip. Average Length: 5/16" [7.9 mm.]. Color: Very yellow green [115. v.YG] becoming Dark grayish red [20. d.gy.R] with maturity.

*Glands.*—Number: 2 to 4 per leaf. Position: Alternately positioned on petiole and base of blade. Size: Medium. Form: Reniform. Color: Strong yellow green [117. s.YG] becoming Moderate reddish brown [43. m.rBr] in the center with age.

*Leaf buds.*—Pointed, medium in size.

Flower buds:

*Hardiness.*—Hardy, with respect to central California winters.

*Diameter.*—Typically 5/16" [7.9 mm.] 1 week before bloom.

*Length.*—Typically 7/16" [11.1 mm.] 1 week before bloom.

*Form.*—Not appressed.
*Surface.*—Pubescent.
*Color.*—Deep pink [3. deep Pk].

Flowers: Perfect, complete, perigynous, usually a single pistil, about 24 stamens, five sepal and petal locations alternately positioned.
*Type.*—Small.
*Average flower diameter.*—⅞" [22.2 mm.].
*Number of petals.*—Five, extra petal fragments are rare.
*Petal shape.*—Oval.
*Petal margin.*—Wavy.
*Average petal diameter.*—⅜" [9.5 mm.].
*Average petal length.*—½" [12.7 mm.].
*Petal apex.*—Rounded.
*Petal base.*—Acute to acuminate.
*Petal color.*—Strong purplish pink [247. s.pPk] toward the margin and Light purplish pink [249. l.pPk] toward the center on both sides.
*Anther color.*—Strong reddish orange [35. s.rO] over a Brilliant orange yellow [67. brill.OY] center, occasionally protruding out of the bud before flower opening.
*Stigma color.*—Pale greenish yellow [104. p.gY].
*Sepal color.*—Grayish purplish red [262. gy.pR].
*Sepal length.*—¼" [6.4 mm.].
*Sepal width.*—3/16" [4.8 mm.].
*Average pistil length.*—⅝" [15.9 mm.], occasionally protruding out of the bud before onset of bloom.
*Average stamen length.*—7/16" [11.1 mm.].
*Fragrance.*—Moderate.
*Blooming period.*—Medium to late, two days after 'Giant Pearl' (U.S. Plant Pat. No. 14,240) nectarine.
*Onset of bloom.*—One percent on Mar. 9, 2013.
*Date of full bloom.*—Mar. 17, 2013.
*Duration of bloom.*—One to two weeks, dependent on ambient temperature.
*Number per cluster.*—1 to 3 with single flowers most common.

FRUIT

Maturity when described: Firm ripe, Sep. 6, 2013.
Date of first picking: Sep. 1, 2013.
Date of last picking: Sep. 11, 2013.
Size: Uniform, medium.
*Average diameter axially.*—3" [76.2 mm.].
*Average diameter across cheek plane.*—2⅞" [73 mm.].
*Average diameter across suture plane.*—2⅞" [73 mm.].
*Typical weight.*—8.2 ounces [232 grams].
Form: Somewhat variable, mostly globose, some slightly asymmetrical.
*Longitudinal section form.*—Round to oval.
*Transverse section through diameter.*—Round.
Suture: Extends from the base, continues along the side, and ends just past the pistil point.
*Near the base.*—A sharp groove.
*Along the side.*—A shallow trough.
*Near the apex.*—A deep groove.
Ventral surface: Rounded, lipped toward the apex on both sides.
Lips: Slightly unequal.
Cavity: Flaring, elongated in the suture plane, suture showing on one side, Pale greenish yellow [104. p.gY] stem markings typical.
*Depth.*—¾" [19.1 mm.].
*Breadth.*—1¾" [44.5 mm.].
Base: Truncate.
Apex: Rounded, cordate if viewed parallel to the suture.
Pistil point: Oblique, mostly depressed within the suture.
Stem: Medium.
*Average length.*—⅜" [9.5 mm.].
*Average width.*—3/16" [4.8 mm.].
Skin:
*Thickness.*—Medium.
*Surface.*—Smooth.
*Tenacity.*—Tenacious to flesh.
*Astringency.*—Nonastringent.
*Tendency to crack.*—None observed in a dry season.
*Color.*—Dark red [16. d.R] over a Dark Pink [6. d.Pk] background with some Yellowish white [92. yWhite] areas where protected from the sun. Moderate Pale yellow [89. p.Y] freckling toward the apex.
Flesh:
*Color.*—White [263. White] with Dark red [16. d.R] streaking next to the stone.
*Surface of pit cavity.*—Covered with Very deep red [14. v.deep R] broken fibers when twisted from the stone.
*Amygdalin.*—Slight.
*Juice.*—Abundant, rich.
*Texture.*—Firm, crisp, melting.
*Fibers.*—Abundant, fine.
*Ripens.*—Slightly earlier at the apex.
*Flavor.*—A very sweet with low acid balance, typically 18-20 brix.
*Aroma.*—Very slight.
*Eating quality.*—Very good.

STONE

Type: Clingstone.
Form: Oval.
Hilum: Narrow.
Base: Rounded to truncate.
Apex: Acuminate.
Sides: Equal.
Surface: Irregularly furrowed near the apex, pitted toward the base.
Ridges: Jagged.
External color: Dark reddish brown [44. d.rBr].
Pit wall color when cracked: Light brown [57. l.Br].
Cavity surface color: Strong yellowish brown [74. s.yBr].
Average pit wall thickness: ¼" [6.4 mm.].
Average width: 1⅛" [28.6 mm.].
Average length: 1¾" [44.5 mm.].
Average breadth: ⅞" [22.2 mm].
Tendency to split: Very slight.
Kernel:
*Form.*—Oval.
*Skin color.*—Strong yellowish brown [74. s.yBr] when first removed.
*Pellicle color.*—Grayish brown [61. gy.Br].
*Vein color.*—Grayish brown [61. gy.Br].
*Taste.*—Bitter.
*Viable.*—Yes.
*Average width.*—9/16" [14.3 mm.].
*Average length.*—15/16" [23.8 mm.]
*Amygdalin.*—Abundant. .

USE

Market: Fresh market and long distance shipping.

Keeping quality: Good, fruit quality observed to remain in good condition after 21 days in standard cold room at 36° Fahrenheit [2° Celsius].

Shipping quality: Good.

Resistance to insects: No unusual susceptibilities noted.

Resistance to diseases: No unusual susceptibilities noted.

OTHER NOTES

Although the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of nectarine tree, substantially as illustrated and described, that is most similar to 'Pearlicious XVII' (U.S. Plant Pat. No. 24,835) nectarine by being a medium size tree, by being self-fruitful, and by producing nectarines that are firm, mostly red in skin color, white in flesh color, sweet in flavor, globose in shape, and clingstone in type, but is distinguished therefrom by having a small blossom instead of large and by producing fruit that has a bitter instead of sweet kernel and that matures about one week later when compared side by side during the same year.

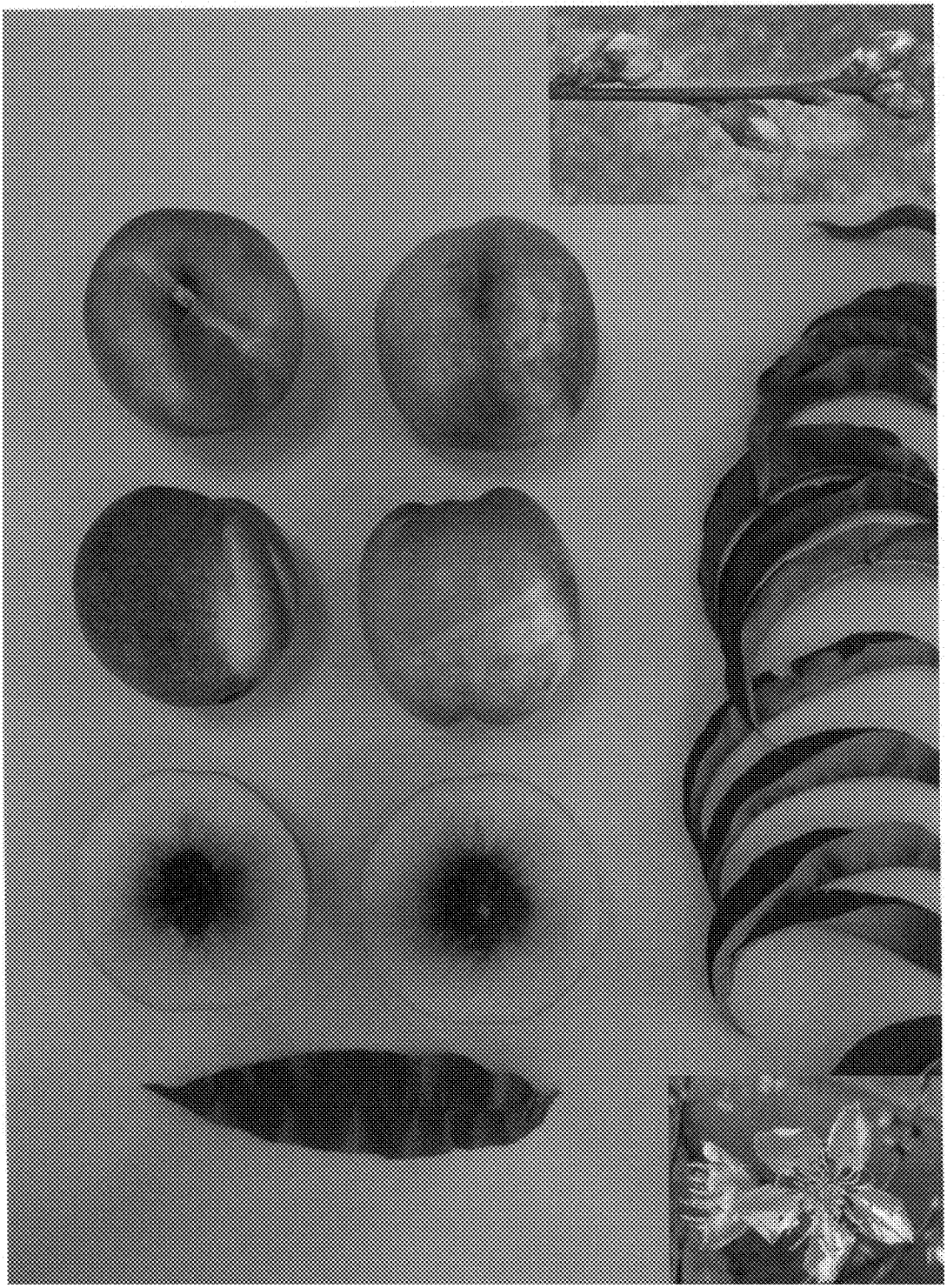

* * * * *